United States Patent [19]
Sherer

[11] Patent Number: 5,298,021
[45] Date of Patent: Mar. 29, 1994

[54] ACLS INFUSION PUMP SYSTEM

[76] Inventor: David J. Sherer, 8520 W. Howell Rd., Bethesda, Md. 20817

[21] Appl. No.: 950,281

[22] Filed: Sep. 24, 1992

[51] Int. Cl.$^5$ .................... A61M 31/00; G06F 15/00
[52] U.S. Cl. ......................... 604/66; 604/50; 128/DIG. 12; 364/413.02
[58] Field of Search ...................... 604/65–67, 604/50; 128/DIG. 12, DIG. 13; 364/413.02, 413.03

[56] References Cited
U.S. PATENT DOCUMENTS

| | | | |
|---|---|---|---|
| 4,220,999 | 9/1980 | Reichlin et al. | 364/413.02 |
| 4,347,851 | 9/1982 | Jundanian | 364/413.02 |
| 4,392,849 | 7/1983 | Petre et al. | 604/66 |
| 4,551,133 | 11/1985 | Zegers de Beyl et al. | 604/67 |
| 4,589,372 | 5/1986 | Smith | 604/66 |
| 4,756,706 | 7/1988 | Kerns et al. | 128/DIG. 13 |
| 4,850,972 | 7/1989 | Schulman et al. | |
| 4,869,266 | 9/1989 | Taylor et al. | |
| 4,933,843 | 6/1990 | Scheller et al. | 604/66 |
| 5,002,055 | 3/1991 | Merki et al. | 604/66 |
| 5,041,086 | 8/1991 | Koening | |
| 5,088,981 | 2/1992 | Howson et al. | |
| 5,100,380 | 3/1992 | Epstein et al. | 604/67 |
| 5,153,827 | 10/1992 | Coutré et al. | 604/66 |

OTHER PUBLICATIONS

Vivian T. Biggers, *Codes for a Code*, American Journal of Nursing, May 1992, pp. 57–61.
Medex advertisement, Anesthesiology News, Aug. 1992, p. 47.
MDE advertisement, Anesthesiology News, Aug. 1992, p. 13.

*Primary Examiner*—Ralph Lewis
*Attorney, Agent, or Firm*—Richard C. Litman

[57] ABSTRACT

An infusion pump system provides a display to indicate to the physician the proper advanced cardiac life support (ACLS) procedures for a given protocol of ACLS heart disorder. The infusion pump is to be located by the bed side of a patient in critical care, such as in the intensive care unit of a hospital. The system monitors certain physiological characteristics as sounds an alarm if any of the measured characteristics have values outside of an acceptable range for each characteristic measured. The infusion pump system would be connected to the patient via an intravenous connection when it is determined that the ACLS procedure is to be administered. By pressing certain buttons, therapeutic agents are administered to the patient. A complete record of the heart activity, the blood pressure, and the oxygen saturation of hemoglobin of the patient, along with which drugs were administered and in what amounts, is continually printed out during the ACLS procedure.

14 Claims, 7 Drawing Sheets

ACLS INFUSION PUMP SYSTEM

BACKGROUND OF THE INVENTION

1. Field of the Invention

The present invention relates to infusion pump systems for delivering a plurality of therapeutic agents to a patient via intravenous connection. More particularly, the present invention relates to an infusion pump system in which critical care therapeutic agents are delivered accurately and rapidly to a patient requiring Advanced Cardiac Life Support (ACLS).

2. Description of the Prior Art

The intravenous delivery of drugs by infusion pump is well known and has many advantages over the manual modes for delivering drugs. However, despite these developments, there remains a need for improved techniques for rapid, safe, and accurate intravenous drug delivery to a patient during ACLS. Presently, the manual mode of operation is still in use for the delivery of therapeutic agents such as lidocaine, sodium bicarbonate, epinephrine, etc. These drugs are used during resuscitation of patients who have sustained cardiac arrest, ventricular tachycardia, ventricular fibrillation, electromechanical dissociation of the heart and pulse, and bradycardia.

To the present day, the nurses and physicians involved in ACLS must locate the separate medications (generally located in a cart which may be locked), take them out of their cardboard containers after removing them from the cart, assemble the syringes, uncap the needles, locate the intravenous injection hub, and, finally, administer the prescribed therapeutic agents.

This procedure wastes precious time, allows for errors in dosing, and increases the risk of the physicians or nurses sticking themselves with a needle due to the rush of providing the therapeutic agents to the patient because of the urgency of the situation. Further, because of the rush and urgency of the situation, records of what drugs were administered and when may not be properly kept or easily remembered afterwards.

An article by Vivian T. Biggers, *Codes for a Code*, American Journal of Nursing, May 1992, pages 57-61, discloses the currently accepted protocols for managing a variety of cardiac emergencies and is incorporated herein by reference, for purposes of indicating the background of the invention and illustrating the state of the art as to the just mentioned protocols. In the ideal situation, a doctor would be thoroughly familiar with these protocols before they are needed in a medical emergency.

The Medex advertisement discloses an infusion pump which delivers the proper amount of the therapeutic agent in accordance with the patient's weight.

The Medical Data Electronics advertisement discloses a portable and compact EKG machine which displays heart rhythm, blood pressure, and oximetry data.

U.S. Pat. No. 5,088,981 issued Feb. 18, 1992 to Howson et al discloses a microprocessor controlled infusion pump system for delivering therapeutic agents in accordance with a "library" of delivery protocols stored in the microprocessor.

U.S. Pat. No. 4,869,266 issued Sep. 26, 1989 to Taylor et al discloses a patient weight monitoring system for controlling an infusion pump, a display, a printer, and for setting off an alarm if the patient's weight changes drastically.

U.S. Pat. No. 4,850,972 issued Jul. 25, 1989 to Schulman et al discloses a programmable infusion pump system for delivering a plurality of therapeutic agents. The system is compact and utilizes a printer to record the history of the activity of the system while in use.

U.S. Pat. No. 5,041,086 issued Aug. 20, 1991 to Koening et al discloses an infusion pump system with Light-Emitting Diodes (LEDs) or a Liquid Crystal Display (LCD) which allows the user to control the system through user inputs.

None of the above inventions and patents, taken either singly or in combination, is seen to describe the instant invention as claimed.

SUMMARY OF THE INVENTION

The present invention utilizes an automated infusion pump system to deliver the required therapeutic agents for patient resuscitation during ACLS. The infusion pump system would be located at the bedside of a patient in critical care, e.g., a patient in an intensive care unit of a hospital. The infusion pump system would monitor the condition of the patient, and when ACLS is deemed necessary, an alert signal is generated. All therapeutic agents are administered at the instructions of the physician by pushing a button located on the outer housing of the system. A display is used to indicate to the physician the standard ACLS procedures in accordance with the protocol associated with the diagnosis made by the physician. The system would prompt the doctor for a diagnosis, i.e., ventricular tachycardia, ventricular fibrillation, etc, and then display steps to be taken in accordance with the established ACLS code. The system would also include an EKG machine to monitor and display the patients heart activity. Other information provided by the system would include the oxygen saturation of hemoglobin of the blood as well as the blood pressure of the patient. By presetting acceptable limits for blood pressure, EKG activity, and oxygen saturation of hemoglobin of the blood, an alert signal, as discussed above, would be generated whenever any one of the above physiologic characteristics are not within their acceptable limits.

During the ACLS procedure, the display is used to prompt and direct the activities of the physician in the automatic mode. However, the administering of the therapeutic agent is not automated in the preferred embodiment. In the automatic mode of operation, the infusion pump system will prompt the doctor for an initial diagnosis as mentioned above. Once the initial diagnosis is entered into the system, the system branches to the proper routine for the condition of the patient as indicated by the physician's diagnosis entered into the system.

The system may prompt the physician for certain physiological characteristics of the patient, e.g., no pulse. If the system disagrees with the physician's observations, the system may prompt the doctor to check again and be sure. However, the decision of what therapeutic drugs to administer and when is left totally to the discretion of the physician. A complete record of the therapeutic agents administered as well as certain physiological characteristics of the patient are printed out. Along with this data, the physicians actions, when those actions took place, and the circumstances which prompted those actions are also printed out.

Accordingly, it is a principal object of the invention to provide a quick mode of response during ACLS by providing the necessary therapeutic agents to the patient at the touch of a button once an intravenous (IV) connection to the patient is made.

It is another object of the invention to provide accurate dosing of the therapeutic agents.

It is an object of the invention to provide instructions to the physician in an automatic mode of operation of the system.

It is a further object of the invention to reduce the risk of needle sticking injuries since all drugs are administered through an IV connection.

Still another object of the invention is to provide complete sequential documentation of the drugs administered, the time they were given, the dosages they were given in, and certain physiological characteristics of the patient at the time they were given.

It is an object of the invention to provide improved elements and arrangements thereof in an apparatus for the purposes described which is inexpensive, dependable, compact, and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
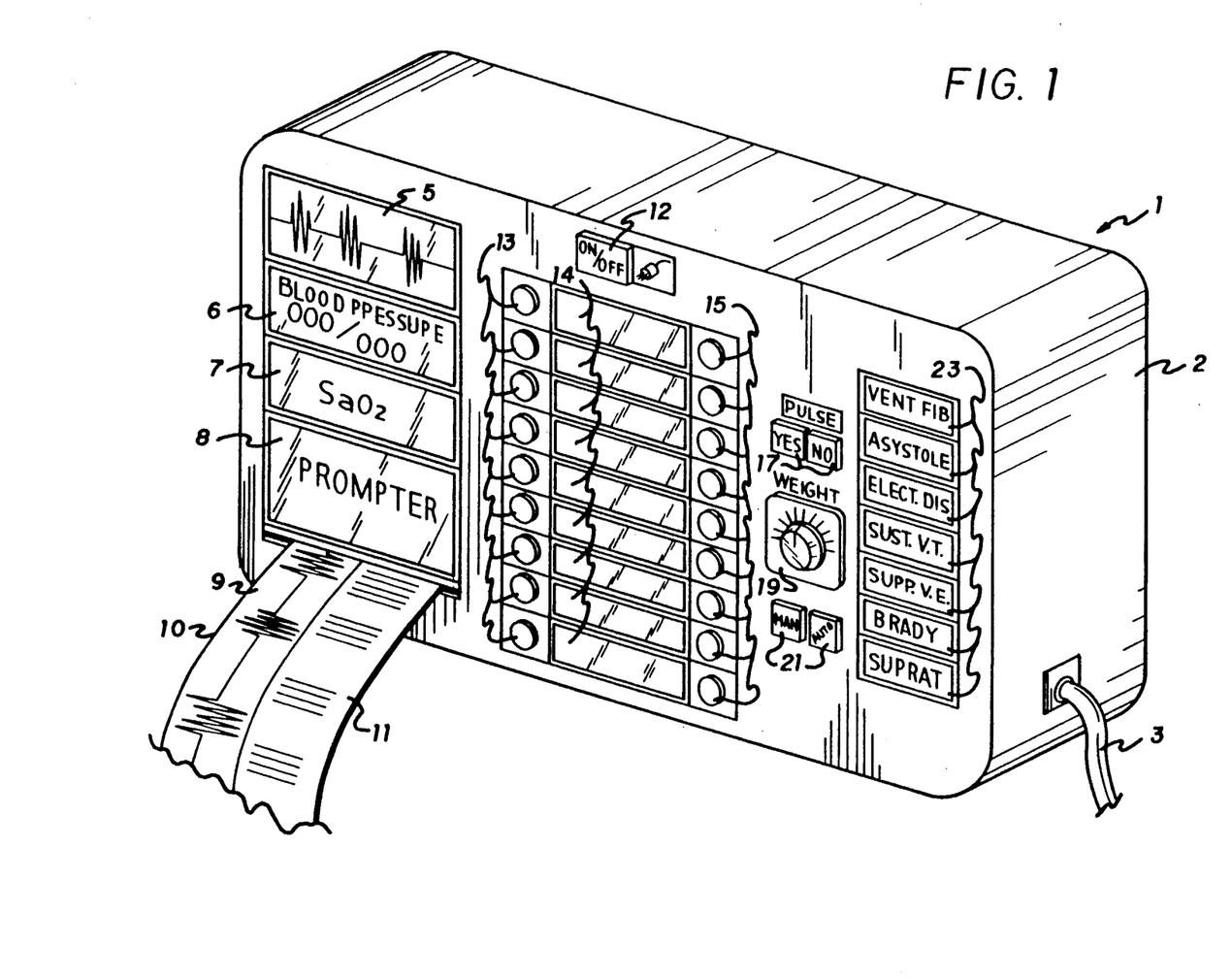
FIG. 1 is perspective view of the present invention.

FIG. 1 shows the ACLS infusion pump system 1 of the present invention. The infusion pump system 1 delivers therapeutic agents to a patient via an intravenous connection (not shown). the delivery mechanisms for the infusion pump system 1 of the preferred embodiment would use independent drivers to deliver therapeutic agents from a syringe into a common channel leading to the intravenous connection to the patient. Howson et al made of record discloses such a system and is herein incorporated by reference.

The syringes containing the various medications which can be delivered to the patient (not shown) are contained within the outer housing 2 of the infusion pump system 1. On the outer face of the housing 2 are located a plurality of buttons 13 for allowing a user, generally the physician or one of his/her assistants, to control the drug delivery controller 55. Each button 13 controls a switch connected to a controller 41 for indicating a particular therapeutic agent to be delivered (see FIG. 2). LCD displays 14 beside the buttons 13 indicate the drugs which will be delivered upon pressing the various buttons 13. If a drug is to be delivered as a function of the weight of the patient, the weight of the patient is indicated to the infusion pump system 1 by a dial 19. If a drug may be delivered in two amounts, a series of buttons 15 are provided to deliver a greater amount of the drug indicated by LCD 14 beside the button 15 to be pushed than would button 13 also located beside the same LCD 14.

Figure 2:
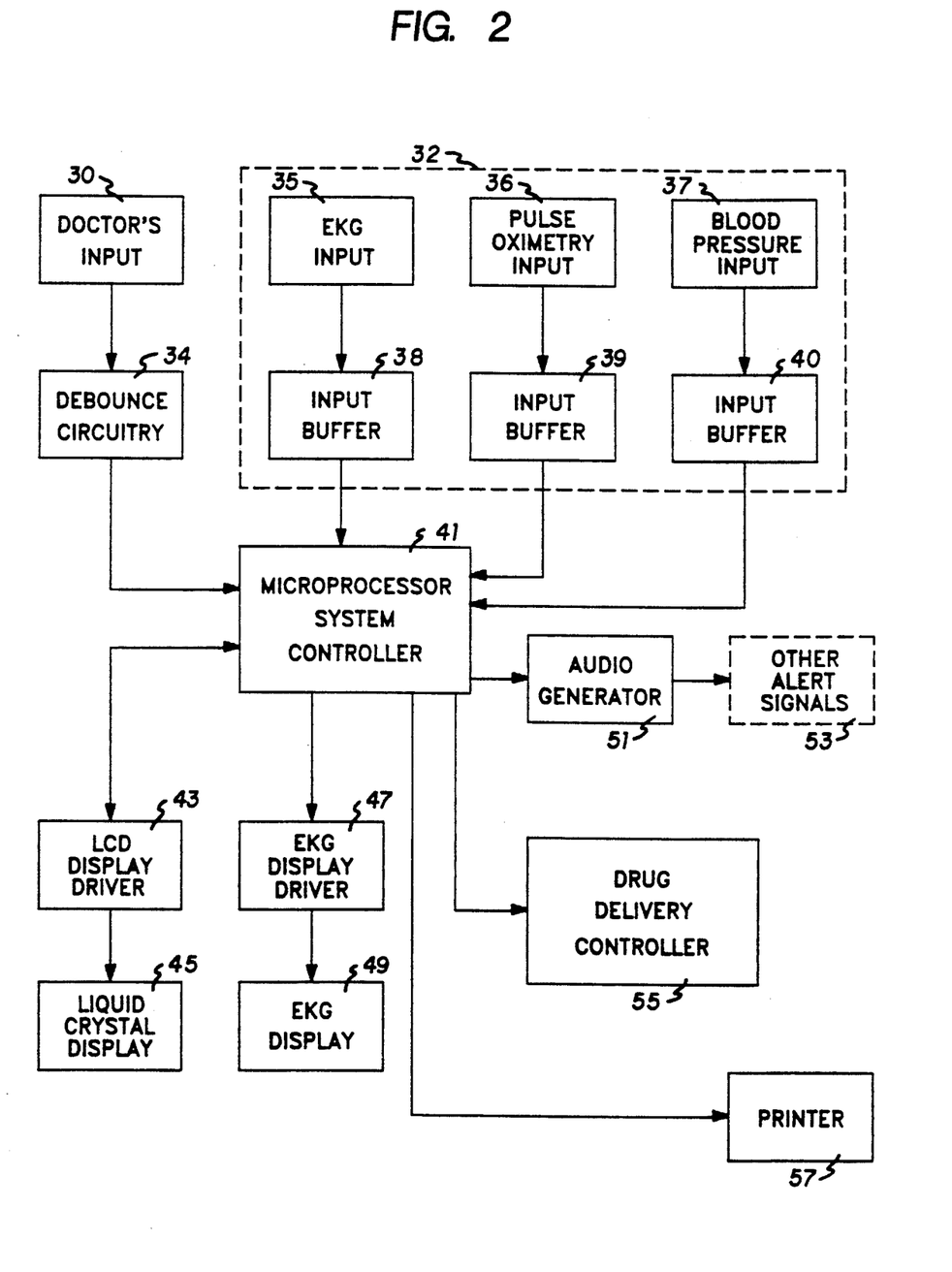
FIG. 2 is a block diagram of the present invention.

In FIG. 2, a block diagram of the circuitry of the infusion pump system 1 is shown. Doctor's inputs 30 includes the input from switches associated with buttons 13, buttons 15, and other inputs discussed below. These doctor's inputs 30 are fed to a microprocessor system controller 41 via debounce circuitry 34 as is well known in the art. Patient data inputs 32 are provided to the controller 41 via certain medical instruments attached to the patient, each of which provide particular physiological data to the controller 41. In the preferred embodiment, the patient data inputs include EKG input data 35 from an electrocardiograph machine connected to the patient, blood pressure input data 37 from a sphygmomanometer connected to the patient, and pulse oximetry input data 36 from a pulse oximeter connected to the patient.

In the preferred embodiment, the infusion pump system 1 would be located at the bedside of a patient and would be plugged in and turned on via on/off switch 12. The device would be monitoring the heart activity, oxygen saturation of hemoglobin of the blood, and the blood pressure from inputs 35, 36, and 37, respectively. The input buffers 38, 39, and 40 connected to the inputs 35, 36, and 37 are input buffers used to convert analog signals received from the various inputs to digital data the microprocessor 41 can understand. The microprocessor monitors the various physiological data provided to it from the patient data inputs 32. The microprocessor compares each piece of physiological data with an acceptable range for the particular physiological characteristic being monitored and activates an audible alarm signal provided by an audio generator 51 and possibly other alert signals 53, such as a light on a console located at a nurses station, if any of the physiological data fall outside of the acceptable range for that physiological characteristic being checked. For example, when checking for blood pressure an acceptable range for the systolic pressure may be from 90 to 130, while an acceptable range for the diastolic pressure may be 60 to 100 as determined by the physician (see below).

As the infusion pump 1 is monitoring the patient, the cardiograph of the patient's heart activity, the blood pressure, and the oxygen saturation of hemoglobin of the blood of the patient are displayed on displays 5, 6, and 7, respectively. From the cardiograph, the infusion pump system 1 can determine the heart rate. When the infusion pump is initially turned on, the physician may input the various acceptable ranges for the physiological characteristics of the patient's input data 32 into microprocessor system. This may be done via buttons 13 and 15 as well as LCD displays 14 when the buttons 21 are set to allow for the automatic mode of operation. For example, the top most display 14 may display diastolic pressure minimum is 60. If the physician wishes to increase this number he/she would press the top most button 15. If the physician wishes to decrease this number he/she would press the top most button 13.

As discussed above, and as shown in FIG. 3, as soon as the infusion pump system 1 is turned on, the device monitors for certain physiological characteristics of the patient to determine if they are within acceptable limits, and, if they are not, alerts medical personnel (see steps 300-310). The prompt display 8, would displays "DIAG?" as shown in step 312 once the physiological characteristics are initially checked. The display 8 continues to display "DIAG?" until a different message is to be displayed. In steps 314-328, the infusion pump system 1 checks for various types doctor's inputs 30 which indicate the doctor's diagnosis.

Figure 3:
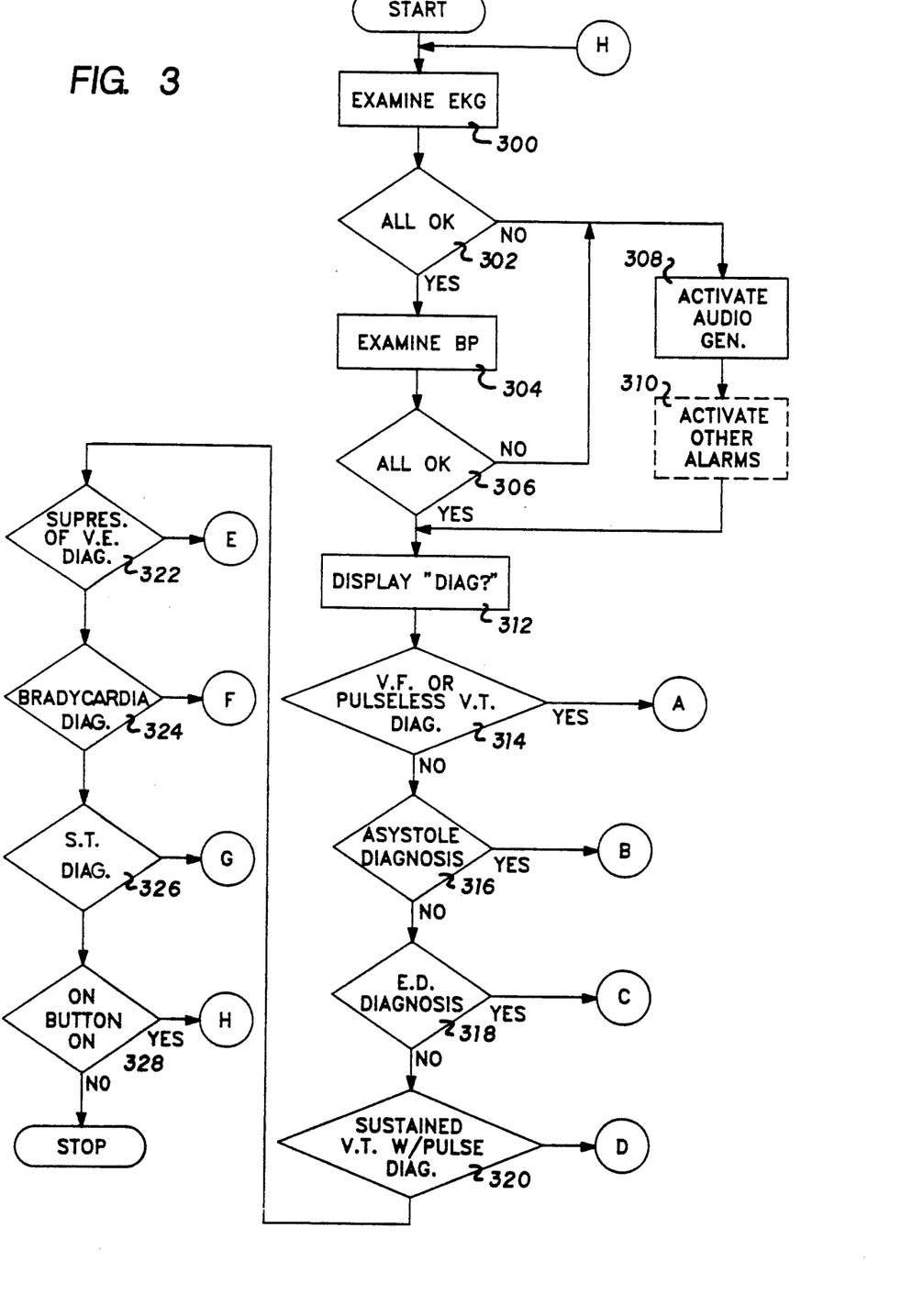
FIGS. 3-7 are flowcharts of the present invention.

When it is determined that the patient does require the ACLS procedure, with the infusion pump system 1 in its automatic mode of operation as set by buttons 21, the physician will indicate on buttons 23 what is his/her diagnosis of the patient's heart disorder. These inputs are part of the doctor's inputs 30 which are fed to the microprocessor system controller 41. If in step 314 it is determined that the doctor has indicated that the patient is experiencing ventricular fibrillation or pulseless ventricular tachycardia, which are treated in the same manner, then the prompt display 8 is controlled to display the question "PULSE?", see step 402 of FIG. 4. The displays 6, 7, 8, and 14 are all part of the liquid crystal displays 45.

The doctor now will indicate whether or not the patient has a pulse via buttons 17. If the doctor indicates that a pulse is detected, from step 404 the system algorithm flows to step 432. If the patient data input 32 is in agreement indicating that the patient does have a pulse, then the system branches to the beginning of the main algorithm of FIG. 3. However, if the patient data input 32 indicates that the patient does not have a pulse, then from step 432 the system performs step 434 and displays on the prompt display 8, "ARE YOU SURE?".

Figure 4:
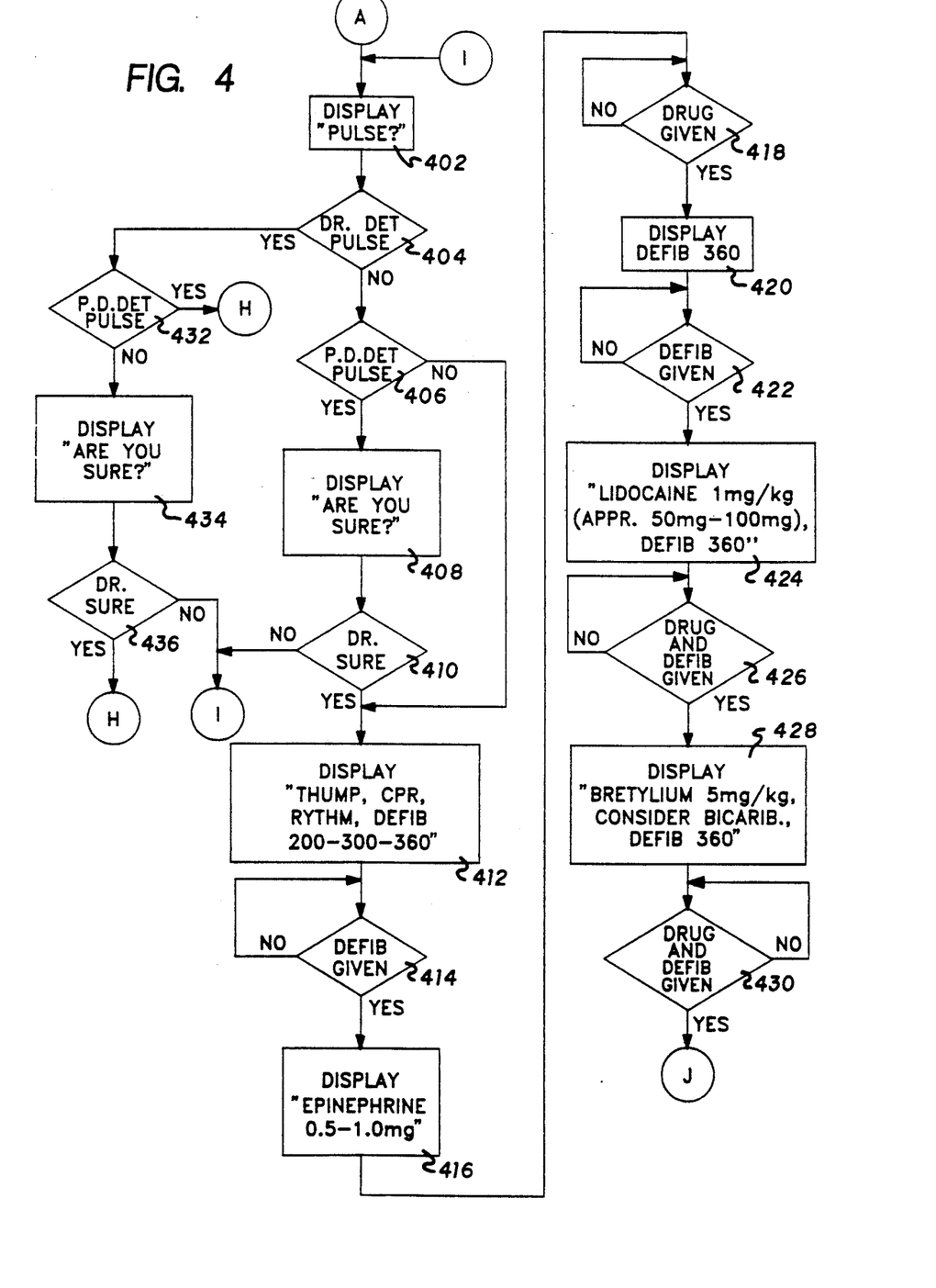
Figure 5:
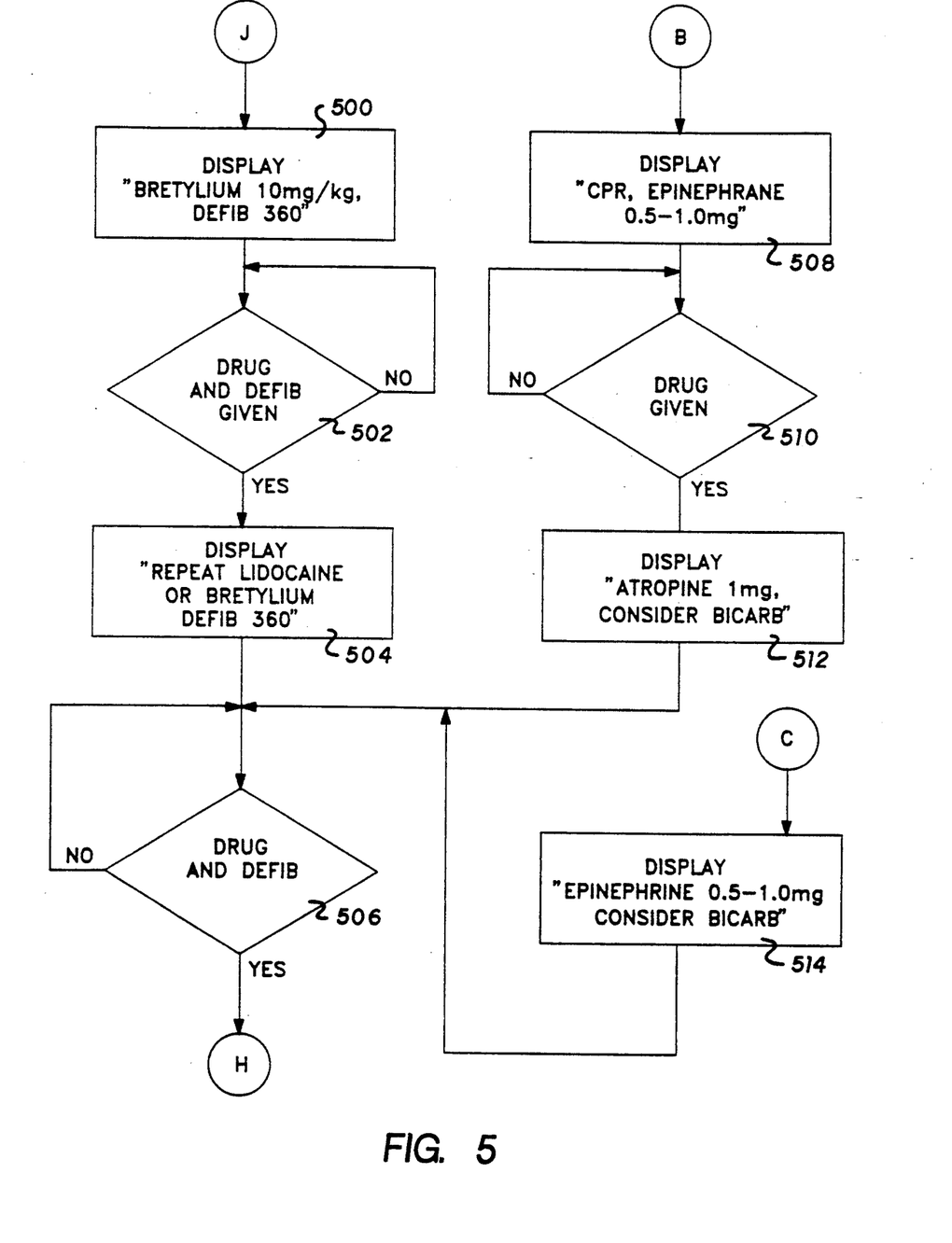
Figure 6:
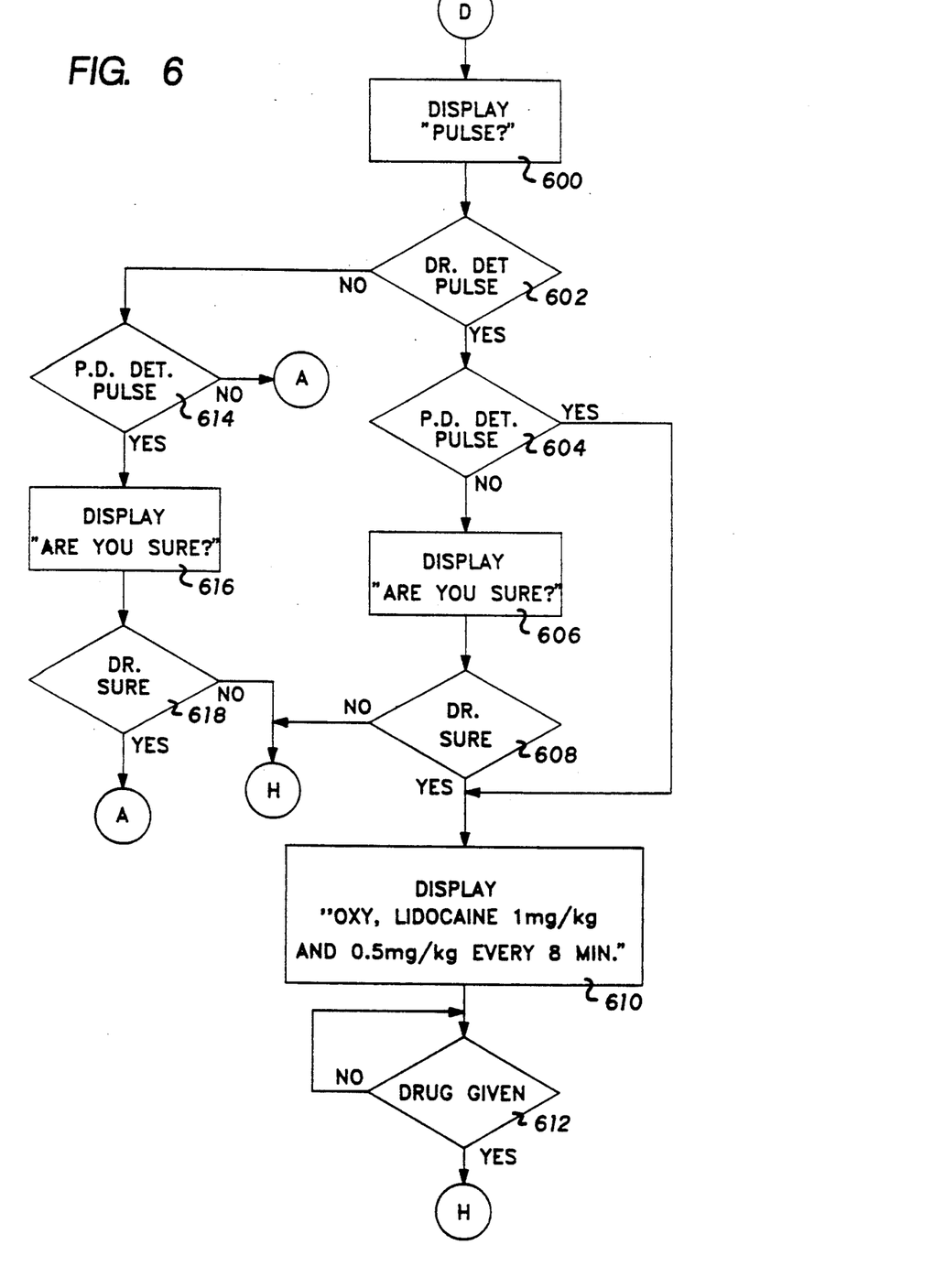
Figure 7:
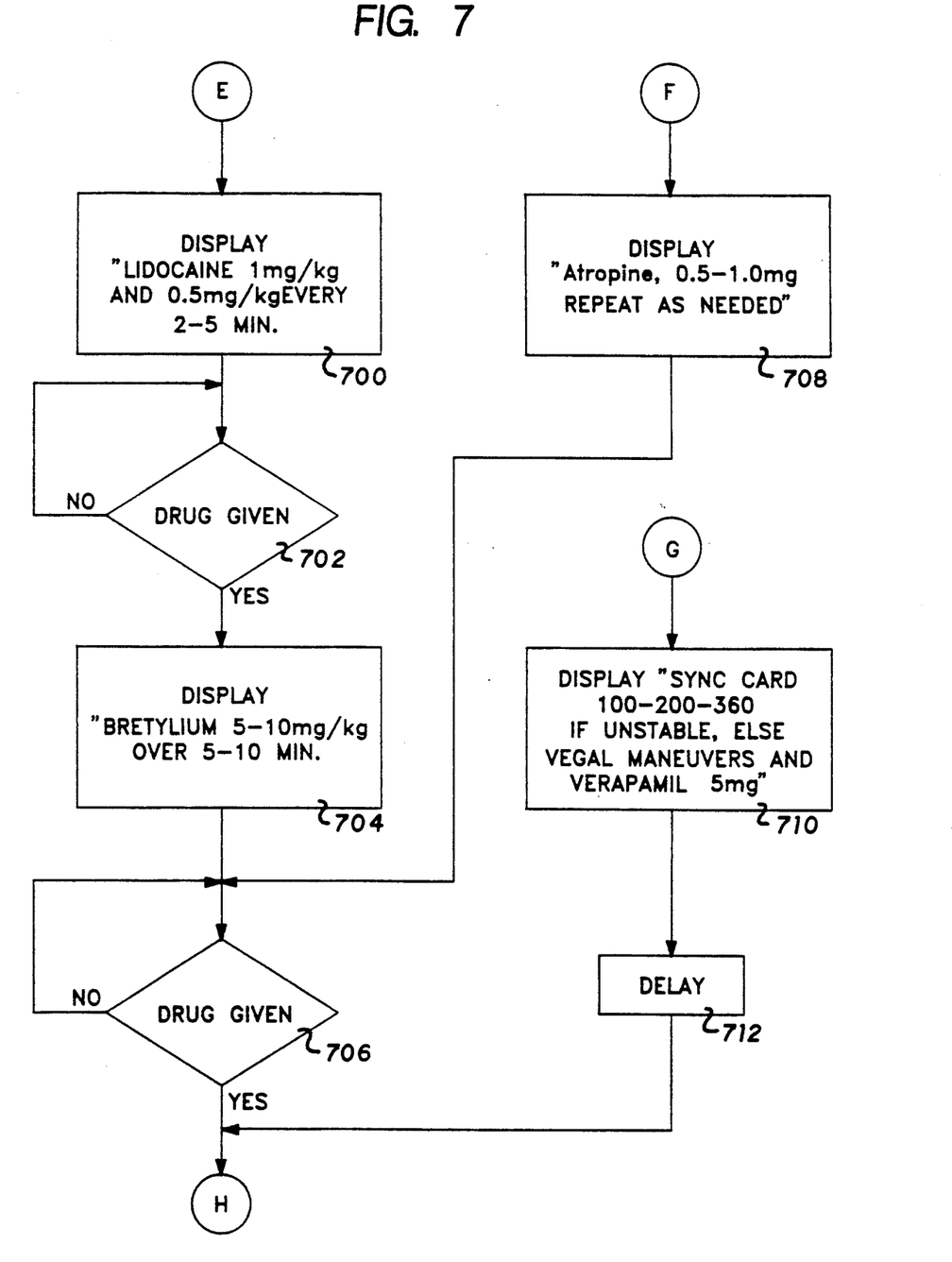

The doctor presses one of the buttons 17 labeled "YES" or "NO" in response to this question (see step 436). If the doctor is sure, the system transfers to step 300, if not, the system transfers to step 402. Again, "PULSE?" is displayed on the prompt display 8, and the doctor presses one of the buttons 17. If the doctor indicates that no pulse is detected, then step 406 of the system's algorithm is performed. If the system 1 detects a pulse, the display 8 prompts "ARE YOU SURE?" in step 408 and then, if the doctor is sure, performs step 412, or if the doctor is not sure, performs step 402. However, if in step 406 no patient pulse is detected by the system, then step 412 is performed next.

In step 412, the prompt display 8 displays "THUMP, CPR, RHYTHM, DEFIB 200-300-360." These are short hand instructions to the doctor to remind the doctor of the proper procedure for ACLS during ventricular fibrillation or pulseless ventricular tachycardia. While the doctor may have all of the ACLS protocol procedures memorized, the prompt display 8 aids the doctor in recalling these procedures. In step 414, the EKG input 35 is monitored by the controller 41 to detect if the defibrillation procedure has been administered. When the system 1 detects that the defibrillation procedure is over, display 8 will indicate that "EPINEPHRINE 0.5-1.0 mg" should be administered to the patient next (step 416). If the physician presses a button 13 next to a display 14 displaying "EPINEPHRINE", then 0.5 milligrams (mg) of epinephrine is administered to the patient. However, if the button 15 next to the display 14 is pushed instead, then 1.0 mg of epinephrine is administered to the patient.

From step 416, the system checks to determine if a button 13 or 15 is pushed in step 418. If so, the display 8 indicates that the next step is to defibrillate the patient with about 360 joules (see step 420). Once the patient is defibrillated as determined in step 422, the display 8 indicates that the next procedure in the ACLS protocol is to administer lidocaine in accordance with the weight of the patient, e.g., 1.0 milligram per kilogram of weight of the patient, and then to defibrillate the patient with 360 joules. The dosage of lidocaine is approximately 50 mg to 100 mg for the weight of the average person. If the weight indicator is not being used, e.g., turned off, then the doctor may press button 13 next to the display 14 displaying "lidocaine" if only 50 mg of lidocaine is to be administered to the patient; otherwise, the button 15 may be pressed directly opposed the same display 14, and 100 mg of lidocaine may be administered to the patient.

Assuming that the weight indicator 19 is not turned off, e.g., set at a value other than zero, then by pressing either button 13 or 15 next to the display 14 indicating the drug "lidocaine", the controller 41 controls the drug delivery controller 55 to deliver the proper dosage of lidocaine by calculating that dosage, e.g. multiplying the value of the weight of the patient in kilograms as indicated by the weight indicator 19, which is one of the doctor inputs 30, by the one (1) to get the number of mg of lidocaine to be delivered by the drug delivery controller 55.

Once lidocaine has been administered to the patient, and the patient has been defibrillated, as detected in step 426, the display 8 will indicate that bretylium at 5 mg per kg weight of the patient should be administered to the patient. Also, the physician should consider giving sodium bicarbonate. The patient should be defibrillated with another 360 joules if the patient is not stabilized at this point (see step 428). Note that the procedure can be terminated by the physician when it is determined by him/her that resuscitation of the patient is no longer necessary, e.g., when the patient has become stabilized. After this last procedure, as indicated in step 428, has been completed as determined in step 430, the system branches back to the main routine in FIG. 3.

While the ACLS is being administered, a tape print out 10 is continually made by the printer 57. This includes the electrocardiograph and well as other data 11 including which therapeutic agents were administered, in what amounts they were administered, and when they were administered. The blood pressure, pulse rate, and oxygen saturation of hemoglobin of the blood are also included in the data 11 along with the time these measurements were made. The print out 10 may be initiated by the microprocessor 41 when the audio warning signal is generated in step 308, or when the physician indicates a diagnosis in steps 314. The print out 10 may be stopped when the on/off button is turned off or it runs out of tape.

In the manual mode of operation, the infusion pump is to be located by the bedside of the patient as it was in the automatic mode of operation. The main routine of FIG. 3 is performed as it was in the automatic mode of operation, except that the steps 314-328 do not cause the system to branch out of the main routine. This is because the prompt display 8 is not used in the manual mode of operation. All the main routine does in the manual mode of operation is monitor the patients physiological characteristics as discussed above and sound an audio alarm and, optionally, other alarms, when any physiological characteristic is outside of an acceptable range.

When the infusion pump system is initially turned on, the displays 14 will allow the doctor to set the values for the acceptable range for each physiological characteristic measured. After a predetermined time elapses from the time the infusion pump system 1 is turned on, the displays indicate which therapeutic agents will be administered when a button 13 or 15 located by it is pushed.

While the infusion pump system 1 is turned on, display 5, which is preferably a miniature cathode ray tube, continually displays the electrocardiograph of the patient as indicated by the EKG input data 35, display 6 continually displays the updated blood pressure as indicated by the blood pressure input data 37, and display 7 continually displays the oxygen saturation of hemoglobin of the blood as indicated and updated by the pulse oximetry input data 36.

Line 3 of FIG. 1 delivers power to the infusion pump system in the preferred embodiment. However, the system 1 could be battery powered by battery cells located within the outer housing 2. The line 3 could also provide external communications lines to change the various parameters of the system 1, such as the acceptable ranges for the various physiological characteristics measured. Also, any external alert signals as generated in the optional step 310 and by the optional block 53 would be connected to the system 1 via line 3.

It is to be understood that the present invention is not limited to the sole embodiment described above, but encompasses any and all embodiments within the scope of the following claims.

I claim:

1. An emergency infusion pump system for the rapid and accurate delivery of therapeutic agents to a patient requiring emergency care comprising:

therapeutic agent delivery means for delivering a plurality of therapeutic agents to the patient via an intravenous connection;

controller means for controlling said therapeutic agent delivery means and including a memory storage area;

a plurality of physiological sensors connected to said controller means;

a plurality of physiological condition continuous displays connected to said controller means, each of said physiological condition continuous displays further connected to one of said physiological sensors and for continuously displaying a sensed physiological condition of the patient;

comparing means for comparing sensed physiological data received from said physiological sensors with acceptable ranges of physiological data stored in said memory storage area;

alarming means for actuating an alarm when the sensed physiological data is not within an acceptable range of physiological data as determined by said comparing means;

a printer connected to said controller means and configured so a continuous printout of each of the sensed physiological conditions, and the time, quantity and name of each therapeutic agent delivered is produced;

protocol display means for displaying a series of instructions in accordance with an emergency code;

display control switching means for selectively setting said emergency infusion pump system in one of a manual mode of operation, wherein said protocol display means is deactivated; and an automatic mode of operation wherein said protocol display means is activated; wherein said protocol display means is further configured for displaying a plurality of protocols in accordance with an established advanced cardiac life support code, each of the protocols being associated with a particular heart disorder a patient may exhibit; and a plurality of diagnostic switches electrically connected to said controller means and configured so a user indicates a diagnosed heart disorder of the patient, each of said diagnostic switches initializes one of said protocols associated with the diagnosed heart disorder so said protocol display means displays only those series of instructions associated with the diagnosed heart disorder of the patient as indicated by the user.

2. An emergency infusion pump system as claimed in claim 1, wherein said physiological sensors comprise at least an electrocardiograph, a blood pressure sensor, and an oximeter.

3. An emergency infusion pump system according to claim 1, wherein said physiological sensors comprise at least an electrocardiograph, a blood pressure sensor, and an oximeter.

4. An emergency infusion pump system for the rapid and accurate delivery of therapeutic agents to a patient requiring emergency care comprising:

therapeutic agent delivery means for delivering a plurality of therapeutic agents to the patient via an intravenous connection;

controller means for controlling said therapeutic agent delivery means and including a memory storage area;

patient sensing means for supplying patient physiological data to said emergency infusion pump system;

patient physiological data continuous display means for continuously displaying the patient physiological data;

comparing means for comparing the patient physiological data received from said patient sensing means with acceptable ranges of physiological data stored in said memory storage area;

alarming means for actuating an alarm when the patient physiological data is not within an acceptable range of physiological data as determined by said comparing means;

a printer connected to said controller means and configured so a continuous printout of the patient physiological data, and the time, quantity and name of each therapeutic agent delivered is produced;

user input means for supplying user observed patient data to said emergency infusion pump system;

querying means for querying the user when the user observed patient data is unequal to the patient physiological data received from said patient sensing means.

5. An emergency infusion pump system as claimed in claim 4, wherein said patient sensing means comprises at least an electrocardiograph, a blood pressure sensor, and an oximeter.

6. An emergency infusion pump system as claimed in claim 5, further comprising:

protocol display means for displaying a series of instructions in accordance with an emergency code; and display control switching means for selectively setting said emergency infusion pump system in one of a manual mode of operation, wherein said protocol display means is deactivated; and an automatic mode of operation wherein said protocol display means is activated.

7. An emergency infusion pump system as claimed in claim 6, wherein said protocol display means is further configured for displaying a plurality of protocols in accordance with an established advanced cardiac life support code, each of the protocols being associated with a particular heart disorder a patient may exhibit, said emergency infusion pump system further comprising:

a plurality of diagnostic switches electrically connected to said controller means and configured so a user indicates a diagnosed heart disorder of the patient, each of said diagnostic switches initializes one of said protocols associated with the diagnosed heart disorder so said protocol display means displays only those series of instructions associated with the diagnosed heart disorder of the patient as indicated by the user.

8. A method of delivering therapeutic agents to a patient requiring emergency care comprising the steps of:

establishing an intravenous connection between a patient and a therapeutic agent delivery system;

continuously sensing and displaying patient physiological data;

comparing the patient physiological data with acceptable ranges of physiological data;

generating an alarm signal when the patient physiological data is not within an acceptable range of physiological data as determined in said comparing step;

diagnosing a patient condition requiring emergency care;

selecting a protocol associated with the diagnosed patient condition from a plurality of protocols;

displaying a series of procedures associated with the selected protocol;

entering user observed patient physiological data associated with the selected protocol into the therapeutic agent delivery system;

querying the user when the user observed patient physiological data is unequal to the sensed patient physiological data as determined in the sensing and displaying step;

delivering one of a plurality of therapeutic agents from the therapeutic agent delivery system to the patient in accordance with the user inputs to the therapeutic agent delivery system; and, displaying a different series of procedures upon delivering a therapeutic agent.

9. A method of delivering therapeutic agents according to claim 8, wherein the therapeutic agent delivery system consists essentially of an emergency infusion pump system.

10. A method of delivering therapeutic agents according to claim 9, further comprising the step of determining the weight of the patient and selectively adjusting the amount of one or more of the therapeutic agents in accordance with the weight of the patient.

11. An emergency infusion pump system for the rapid and accurate delivery of therapeutic agents to a patient requiring emergency care comprising:

therapeutic agent delivery means for delivering a plurality of therapeutic agents to the patient via an intravenous connection;

controller means for controlling said therapeutic agent delivery means and including a memory storage area;

a plurality of physiological sensors connected to said controller means;

a plurality of physiological condition continuous displays connected to said controller means, each of said physiological condition continuous display further connected to one of said physiological sensors and for continuously displaying a sensed physiological condition of the patient;

comparing means for comparing sensed physiological data received from said physiological sensors with acceptable ranges of physiological data stored in said memory storage area;

alarming means for actuating an alarm when the sensed physiological data is not within an acceptable range of physiological data as determined by said comparing means;

a printer connected to said controller means and configured so a continuous printout of each of the sensed physiological conditions, and the time, quantity and name of each therapeutic agent delivered is produced;

user input means for supplying user observed patient data to said emergency infusion pump system;

querying means for querying the user when the user observed patient data is unequal to the patient physiological data received from said physiological sensors.

12. An emergency infusion pump system according to claim 11, further comprising:

protocol display means for displaying a series of instructions in accordance with an emergency code; and display control switching means for selectively setting said emergency infusion pump system in one of a manual mode of operation, wherein said protocol display means is deactivated; and an automatic mode of operation wherein said protocol display means is activated.

13. An emergency infusion pump system according to claim 12, wherein said protocol display means is further configured for displaying a plurality of protocols in accordance with an established advanced cardiac life support code, each of the protocols being associated with a particular heart disorder a patient may exhibit, said emergency infusion pump system further comprising:

a plurality of diagnostic switches electrically connected to said controller means and configured so a user indicates a diagnosed heart disorder of the patient, each of said diagnostic switches initializes one of said protocols associated with the diagnosed heart disorder.

14. An emergency infusion pump system according to claim 13, wherein said physiological sensors comprises at least an electrocardiograph, a blood pressure sensor, and an oximeter.

* * * * *